(12) United States Patent
Davis et al.

(10) Patent No.: US 7,577,473 B2
(45) Date of Patent: *Aug. 18, 2009

(54) APPARATUS FOR SUBCUTANEOUS PLACEMENT OF AN IMAGING MARKER

(75) Inventors: Richard E. Davis, Grand Rapids, MI (US); Ryan L. Goosen, Coopersville, MI (US); Steven E. Field, Grand Rapids, MI (US); Richard M. Chesbrough, Bloomfield Hills, MI (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 283 days.

This patent is subject to a terminal disclaimer.

(21) Appl. No.: 10/906,106

(22) Filed: Feb. 3, 2005

(65) Prior Publication Data

US 2006/0184090 A1 Aug. 17, 2006

(51) Int. Cl.
*A61B 6/00* (2006.01)
*A61B 17/34* (2006.01)

(52) U.S. Cl. ............................. 600/431; 606/185

(58) Field of Classification Search ............... 600/426, 600/431; 606/185; 604/19
See application file for complete search history.

(56) References Cited

U.S. PATENT DOCUMENTS

| | | | |
|---|---|---|---|
| 2,907,327 A | 10/1959 | White | |
| 4,820,267 A | 4/1989 | Harman | |
| 4,994,028 A | 2/1991 | Leonard et al. | |
| 5,250,026 A | 10/1993 | Ehrlich et al. | |
| 5,353,804 A | 10/1994 | Kornberg et al. | |
| 5,542,915 A * | 8/1996 | Edwards et al. | ............... 604/22 |
| 5,842,999 A | 12/1998 | Pruitt et al. | |
| 5,879,357 A | 3/1999 | Heaton et al. | |
| 6,142,955 A | 11/2000 | Farascioni et al. | |
| 6,190,350 B1 | 2/2001 | Davis et al. | |
| 6,261,302 B1 | 7/2001 | Voegele et al. | |
| 6,312,429 B1 | 11/2001 | Burbank et al. | |
| 6,551,253 B2 | 4/2003 | Worm et al. | |
| 6,575,991 B1 * | 6/2003 | Chesbrough et al. | ........ 606/185 |
| 6,638,234 B2 | 10/2003 | Burbank et al. | |
| 6,766,186 B1 | 7/2004 | Hoyns et al. | |
| 2002/0045842 A1 | 4/2002 | Van Bladel et al. | |
| 2002/0095204 A1 | 7/2002 | Thompson et al. | |
| 2004/0127765 A1 | 7/2004 | Seiler et al. | |
| 2004/0162574 A1 | 8/2004 | Viola | |

FOREIGN PATENT DOCUMENTS

EP 0966925 12/1999

* cited by examiner

*Primary Examiner*—Eric F Winakur
*Assistant Examiner*—Michael T Rozanski

(57) ABSTRACT

A subcutaneous marking apparatus for placement of an imaging marker at a predetermined site in a tissue mass comprises a handle having a front portion and a rear portion, a cannula, a stylet slidably received within the cannula, a trigger extending from the front portion of the handle and operably engaging the stylet, and an imaging marker disposed within a marker recess in a distal end of the cannula. A user can firmly grasp the marking apparatus in one hand and simultaneously actuate the trigger with a finger or a thumb of the same hand to move the stylet and thereby place the imaging marker at the predetermined site.

22 Claims, 12 Drawing Sheets

APPARATUS FOR SUBCUTANEOUS PLACEMENT OF AN IMAGING MARKER

FIELD OF THE INVENTION

The invention relates generally to an apparatus for subcutaneous placement of an imaging marker and more particularly to a marking apparatus comprising a trigger extending from a front portion of a handle so that a user can firmly grip the marking apparatus and simultaneously actuate the trigger for accurate placement of an imaging marker.

DESCRIPTION OF THE RELATED ART

Subcutaneous imaging markers are commonly implanted to identify a particular location in various areas and organs of the body. For example, markers are positioned at biopsy sites so that a practitioner can readily identify the tissue sample location after the biopsy procedure is completed. Markers are also used to denote the locations of lesions for therapeutic procedures, such as chemotherapy. Typically, markers located within the body can be viewed by various imaging techniques, such as radiography, ultrasound, and magnetic resonance imaging (MRI).

While the marker is being placed at a predetermined site in a tissue mass, the practitioner typically utilizes an imaging system to view the position of the marking apparatus used to implant the marker so that the marker can be accurately placed at the predetermined site. A commonly used imaging system is an ultrasonic system comprising a wand that is positioned against a patient's skin, and the wand is directed towards the area to be imaged. Ideally, the practitioner holds the ultrasonic wand in one hand and the marking apparatus in the other hand so that he or she can easily adjust either the wand or the marking apparatus when desired. However, prior art marking apparatuses often comprise triggers positioned at the rear or proximal end, and, as a result, it is difficult for the practitioner to establish a firm grasp on the apparatus in one hand and simultaneously deploy the trigger with the same hand to insert the marker. The practitioner can have another person assist, such as by either holding the ultrasonic wand or by deploying the trigger, but involving another person in the process makes the process unnecessarily complex and inefficient and could lead to errors resulting from communication problems. If the practitioner executes the process without assistance, the practitioner can accidentally shift, pivot, or otherwise move the apparatus while awkwardly deploying the trigger to place the marker in the tissue mass. As a result, the imaging marker can be inaccurately implanted, which can be problematic when the practitioner needs to identify the predetermined site in the tissue mass at a later time. Thus, it is desirable for the practitioner to be able to firmly and securely hold the marking apparatus in one hand and simultaneously deploy the trigger with the same hand to accurately position the imaging marker in the tissue mass.

SUMMARY OF THE INVENTION

In one aspect, a subcutaneous marking apparatus according to the invention for placement of an imaging marker at a predetermined site in a tissue mass to facilitate subsequent determination of the predetermined site comprises a handle having a front portion and a rear portion located behind the front portion, with the rear portion having a length such that a user can grasp the handle between multiple fingers and a palm or a thumb of one hand; a cannula defining a lumen and having a proximal end mounted to the handle and a distal end defining a tip; a stylet slidably received within the lumen for movement between a ready position in which a distal end of the stylet is spaced inwardly from the tip to form a marker recess between the distal end of the stylet and the tip, and an extended position in which the distal end of the stylet is advanced toward the tip and into the marker recess; a trigger extending from the front portion and operably engaging the stylet, the trigger being operable between a first position and a second position for moving the stylet between the ready position and the extended position, and an imaging marker disposed within the marker recess. The marking apparatus can place the imaging marker at the predetermined site by the user actuating the trigger between the first and second positions with either an index finger or the thumb of the one hand while holding the handle between either the fingers and the thumb or the fingers and the palm to move the stylet from the ready position to the extended position to thereby eject the imaging marker from the marker recess after the tip of the cannula is located at the predetermined site. The handle can be grasped by at least three fingers of the one hand.

The trigger can be slidably mounted to the front portion such that sliding the trigger serves to operate the trigger between the first and second positions. The trigger can be connected to the stylet. The stylet can be fixedly mounted to the trigger such that movement of the trigger is directly transferred to movement of the stylet.

The marking apparatus can further comprise a first detent to hold the trigger in one of the first and second positions and a second detent for holding the trigger in the other of the first and second positions. The trigger can comprise at least one projection, and the handle can further comprise at least one catch sized to receive the at least one projection to retain the trigger in at least one of the first and second positions. The trigger can further comprise a biasing member that biases the at least one projection into the at least one catch to thereby prevent movement of the trigger from the at least one of the first and second positions.

The handle can further comprise a resilient grip, preferably on the front portion.

In another aspect, a subcutaneous marking apparatus according to the invention for placement of an imaging marker at a predetermined site in a tissue mass to facilitate subsequent determination of the predetermined site comprises a handle to be grasped by one hand of a user and comprising a front portion and a rear portion; a cannula defining a lumen and having a proximal end mounted to the handle and a distal end defining a tip; a stylet slidably received within the lumen for movement between a ready position in which a distal end of the stylet is spaced inwardly from the tip to form a marker recess between the distal end of the stylet and the tip, and an extended position in which the distal end of the stylet is advanced toward the tip and into the marker recess; a trigger extending from the front portion of the handle and connected to the stylet, the trigger being movable between a first position and a second position for moving the stylet between the ready position and the extended position; and an imaging marker disposed within the marker recess. The marking apparatus can place the imaging marker at the predetermined site by the user actuating the trigger between the first and second positions with either an index finger or a thumb of the one hand to move the stylet from the ready position to the extended position to thereby eject the imaging marker from the marker recess after the tip of the cannula is located at the predetermined site.

The handle can be grasped between either fingers and the thumb or the fingers and a palm of the one hand. The handle can be grasped by at least three fingers of the one hand.

The trigger can be slidably mounted to the front portion such that sliding the trigger serves to operate the trigger between the first and second positions. The stylet can be fixedly mounted to the trigger such that movement of the trigger is directly transferred to movement of the stylet.

The marking apparatus can further comprise a first detent to hold the trigger in one of the first and second positions and a second detent for holding the trigger in the other of the first and second positions. The trigger can comprise at least one projection, and the handle can further comprise at least one catch sized to receive the at least one projection to retain the trigger in at least one of the first and second positions. The trigger can further comprise a biasing member that biases the at least one projection into the at least one catch to thereby prevent movement of the trigger from the at least one of the first and second positions.

The handle can further comprise a resilient grip on the front portion.

DESCRIPTION OF THE PREFERRED EMBODIMENT

Figure 1:
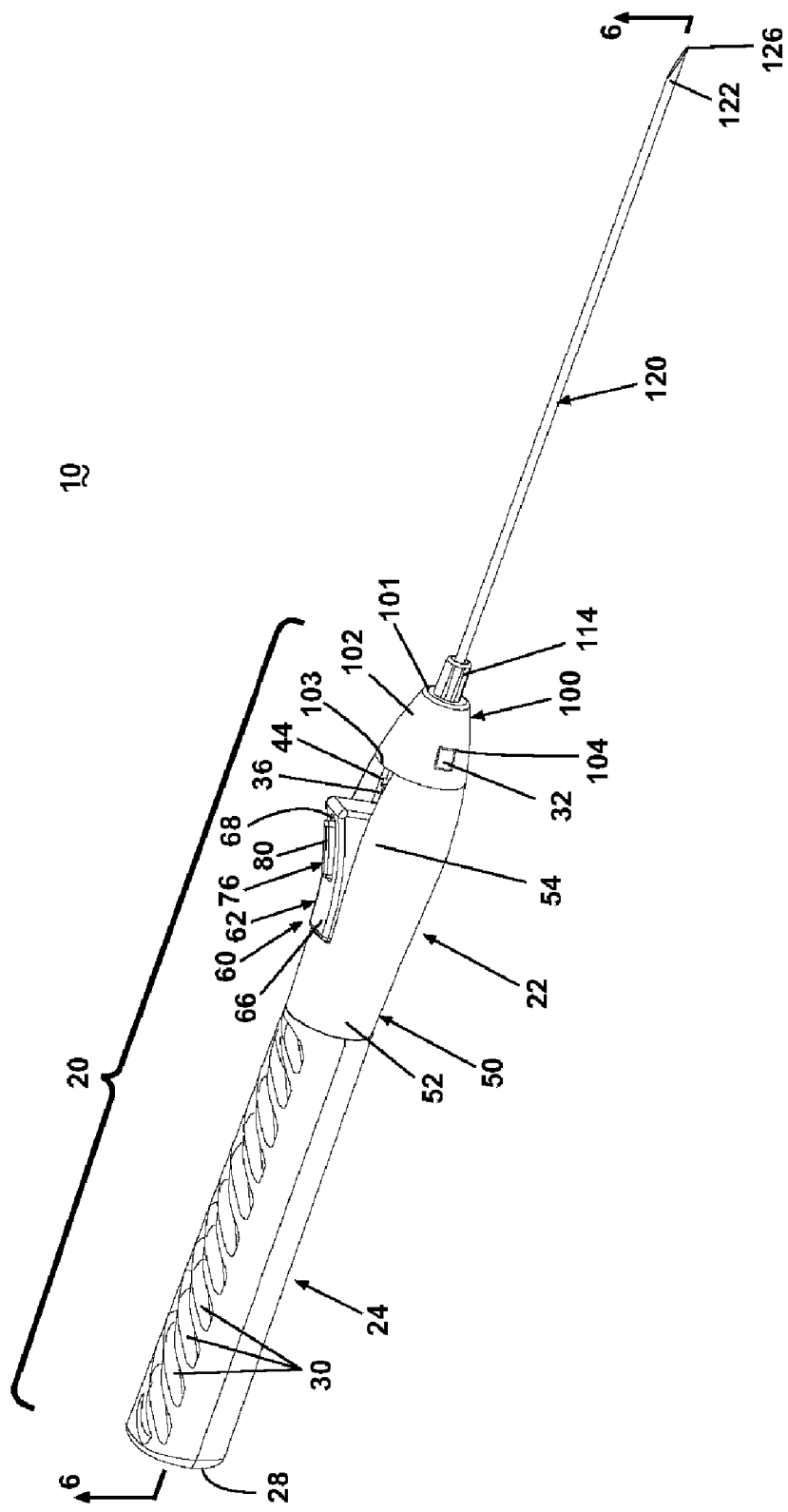
FIG. 1 is a perspective view of the marking apparatus according to the invention and comprising a handle with a trigger in a first position.
Figure 2:
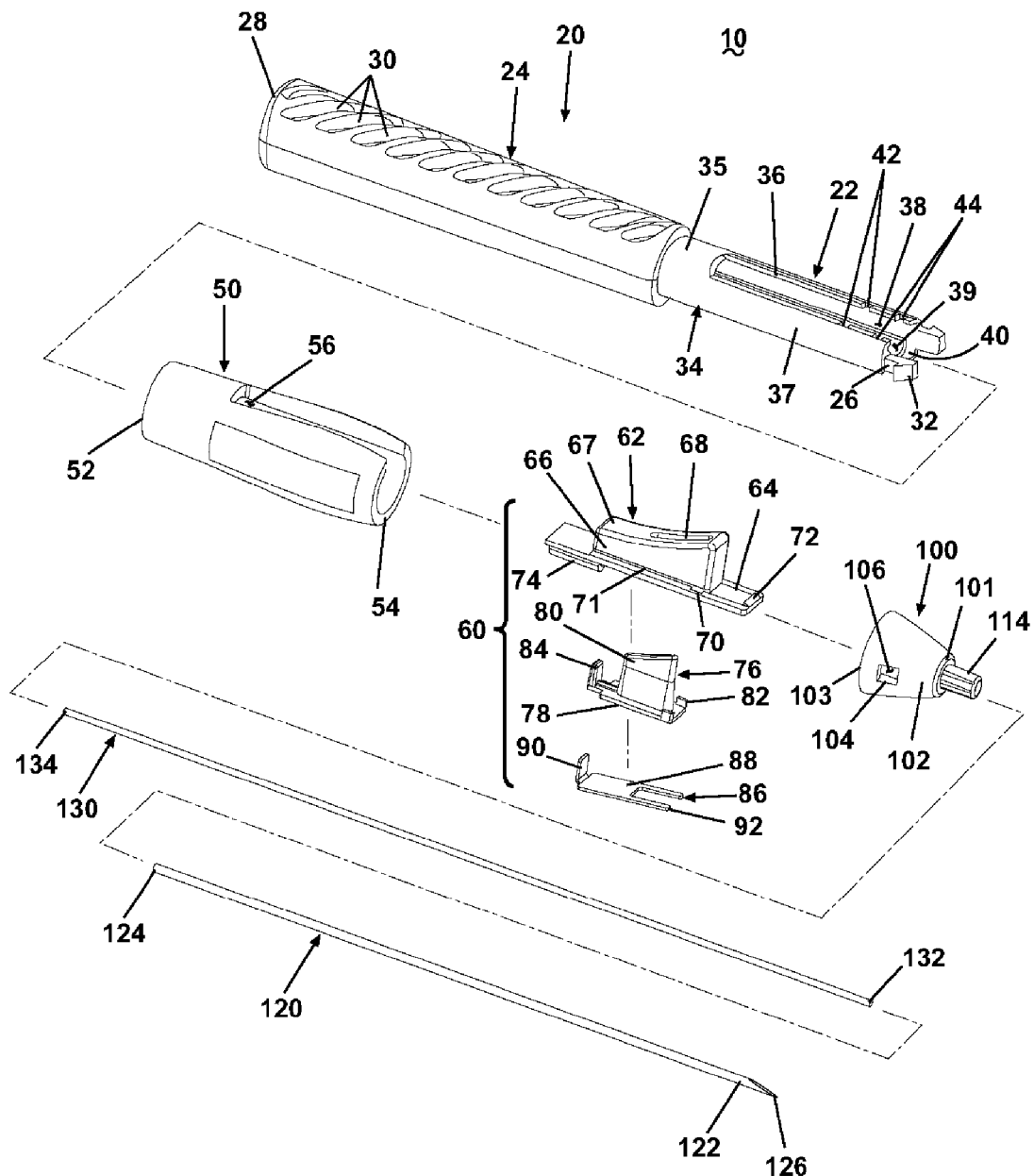
FIG. 2 is an exploded view of a marking apparatus of FIG. 1.

The invention addresses the deficiencies of the prior art and provides a marking apparatus for subcutaneous placement of an imaging marker, wherein the marking apparatus comprises a trigger extending from a front portion of a handle such that a user can firmly grasp the marking apparatus in one hand while deploying the trigger with the same hand to accurately place the imaging marker at a predetermined site.

Referring now to the figures and particularly to FIGS. 1, 2, 6, and 6A, a marking apparatus 10 according to the invention comprises a handle 20 that terminates at a tapered cap 100 and supports a trigger 60 operatively connected to a stylet 130 disposed inside a cannula 120 fixed to the cap 100. For convenience of this description, the cap 100 is described as being separate from the handle 20. However, the cap 100 can be considered as part of the handle 20 and can even be integrated with the handle 20.

Figure 3:
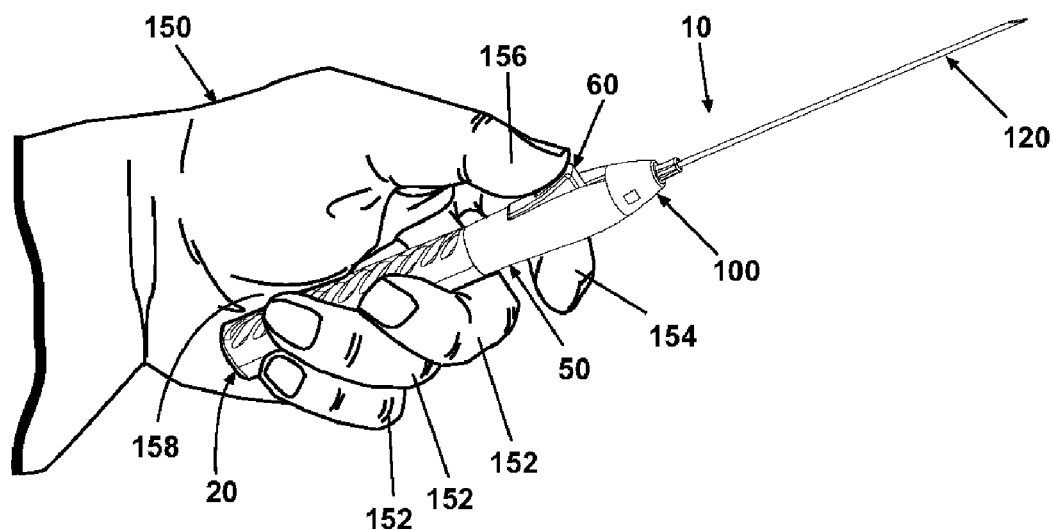
FIG. 3 is a perspective view of the marking apparatus shown in FIG. 1 held in a user's hand in a first manner.
Figure 4:
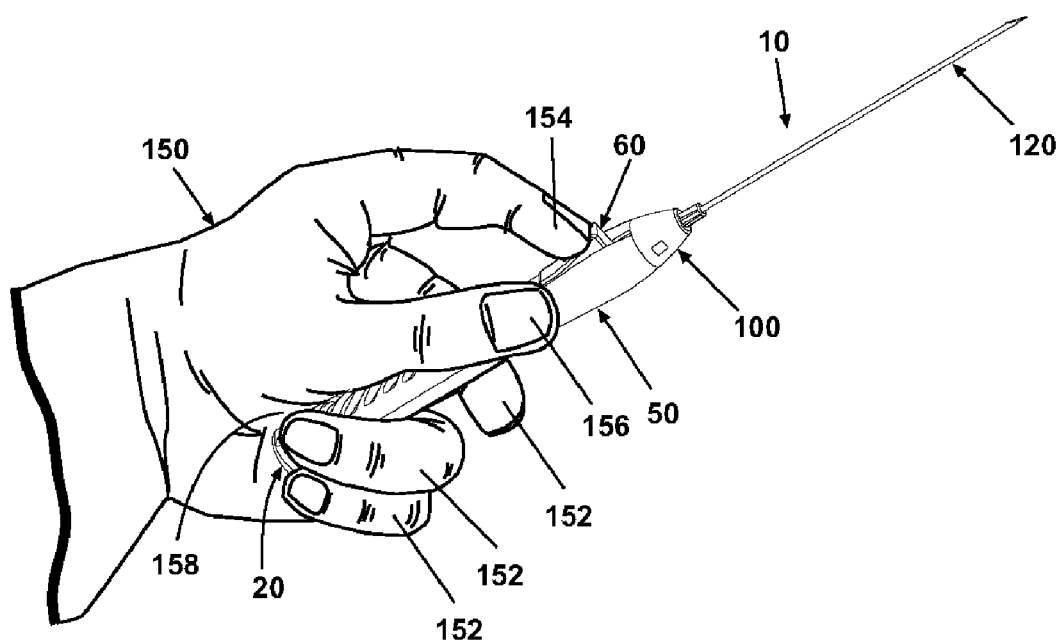
FIG. 4 is a perspective view of the marking apparatus shown in FIG. 1 held in a user's hand in a second manner.
Figure 5:
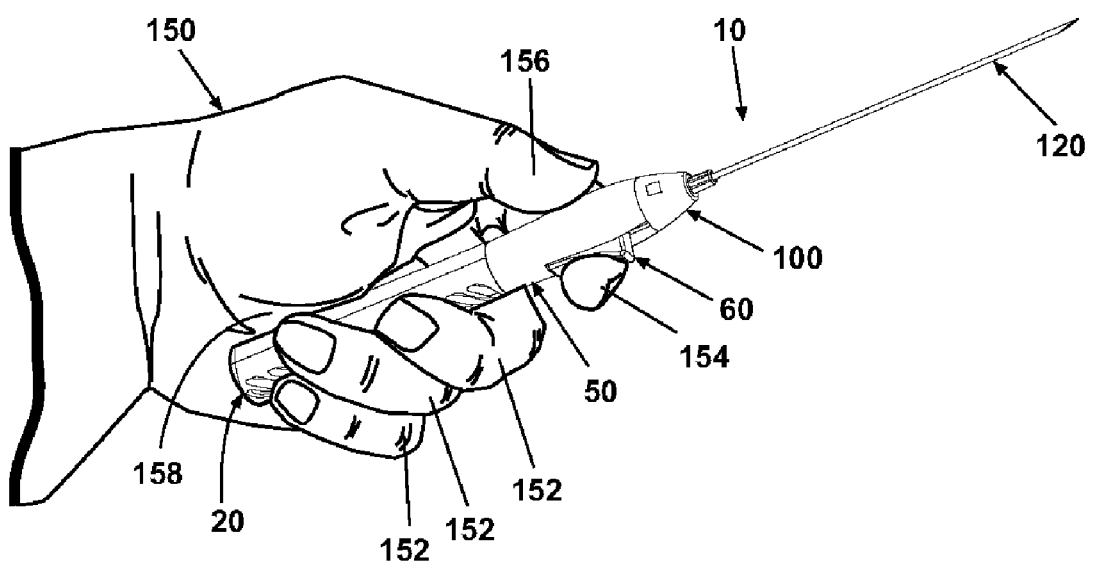
FIG. 5 is a perspective view of the marking apparatus shown in FIG. 1 held in a user's hand in a third manner.

The handle 20 comprises a front portion 22, a rear portion 24, with the front portion defining a distal end 26 for the handle and the rear portion 24 defining a proximal end 28 for the handle. The rear portion 24 is elongated such that the user can grasp the handle 20 between multiple fingers 152 and a palm 158 or a thumb 156 of one hand 150, as shown in FIGS. 3-5 and described in more detail hereinafter. Preferably, the rear portion 24 tapers outward near the distal end 28 to conform to the hand 150 and includes a texture, such as ribbing 30, on its outer surface to facilitate gripping of the handle 20. The front portion 22 comprises a hollow, elongated body 34 having a circular region 35 and an arcuate region 37 with a pair of inwardly extending flanges 36. Within the front portion 22 is an internal cavity 38 defined on one side by a curved lower wall 40 to form a channel 39. The flanges 36 and the cavity 38 slidingly receive the trigger 60, and the flanges 36 include axially spaced notches or detents that form a first set of catches 42 and a second set of catches 44 to retain the trigger 60 in a first position or a second position, respectively, as will be described in more detail hereinafter. The front portion 22 further comprises diametrically opposed terminal clips 32 for mounting the cap 100 to the handle 20.

The relative lengths of the front portion 22 and the rear portion 24 of the handle 20 can vary from that shown in the figures. The relative lengths can be selected based on factors such as comfort, ease of use, and size of the user's hand 150. It is, however, necessary that the rear portion 24 is long enough for the user to grasp the handle 20 between the multiple fingers 152 and the palm 158 or the thumb 156 of the hand 150 and that the front portion 22 is long enough to slidably mount the trigger 60. As used herein, the finger or fingers 152 refers to one or more appendage other than the thumb 156 extending from the hand 150.

The front portion 22 of the handle 20 is surrounded by a grip 50 preferably composed of a resilient material. The grip 50 comprises a proximal region 52 that encircles the circular region 35, a distal region 54 that corresponds to the arcuate region 37, and, within the distal region 54, a slit 56 that is aligned with the flanges 36 to accommodate the trigger 60 through its range of motion. The outer diameter of the front portion 22 of the handle 20 is less than that of the rear portion 24, and the grip 50 is dimensioned, in at least the proximal region 52, in accordance with the difference in the outer diameters so that the grip 50 is flush with the rear portion 24 of the of the handle 20.

With continued reference to FIGS. 1, 2, 6, and 6A, the cap 100 comprises a generally frustoconical body 102 with a hollow interior 106 and diametrically opposed apertures 104 sized to receive the clips 32 on the front portion 22 of the handle 20. The body 102 has a distal end 101 with a nipple 114 to which the cannula 120 is mounted and a proximal end 103 that abuts the front portion 22 of the handle 20 when the cap 100 is coupled with the handle 20. The interior 106 is partially defined by a flat upper wall 108 and a curved lower wall 110. When the cap 100 and the handle 20 are coupled, the flat upper wall 108 is generally coplanar with an underside of the flanges 36, and the curved lower wall 110 aligns with the curved lower wall 40. The cap 100 further comprises a detent 112 in the flat upper wall 108 for receiving a portion of the trigger 60 when the trigger 60 is in the second position, as will be described in more detail hereinafter.

The cannula 120 comprises a proximal end 124 mounted to the cap 100, a distal end 122 defining a tip 126, and a lumen 128 extending between the proximal and distal ends 124 and 122. The tip 126 is preferably pointed for insertion through skin and into the tissue mass; however, the tip 126 can optionally be blunt, for example, if the marking apparatus 10 is utilized with a trocar or the like. Preferably, the cannula 120 is a 17-gage (0.058 inch outer diameter) cannula, with an inner diameter ranging from 0.049 to 0.051 inches. Furthermore, the distal end 122 of the cannula 120 can be designed for enhanced visibility using common imaging techniques, such as radiography, ultrasonography, and magnetic resonance imaging (MRI).

Figure 7:
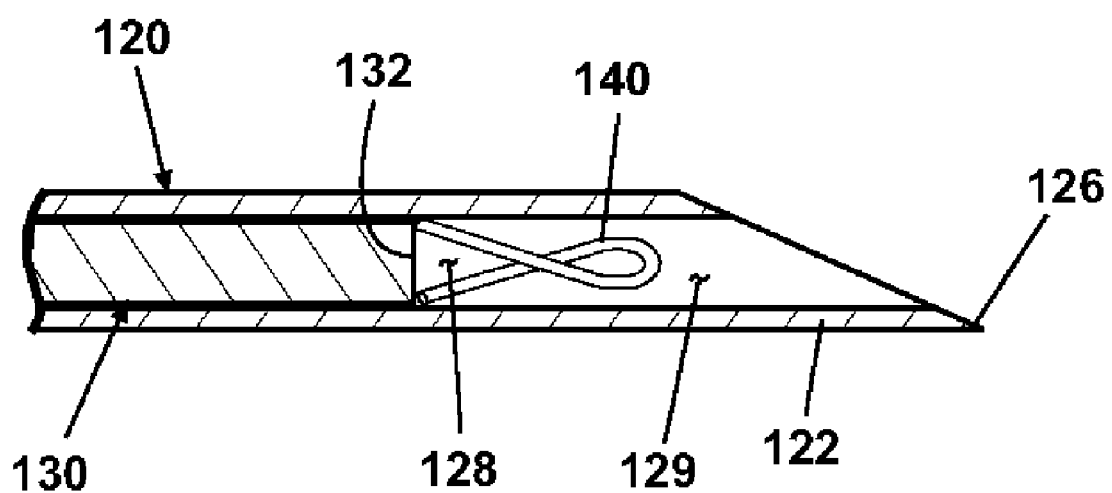
FIG. 7 is enlarged sectional view of the region labeled VII in FIG. 6.
Figure 8:
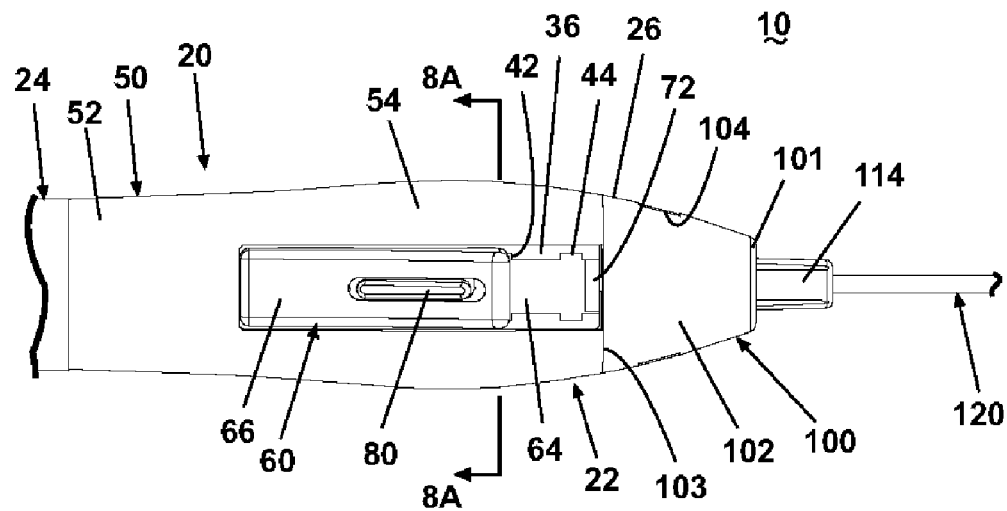
FIG. 8 is a top view of the marking apparatus shown in FIG. 1.
Figure 11:
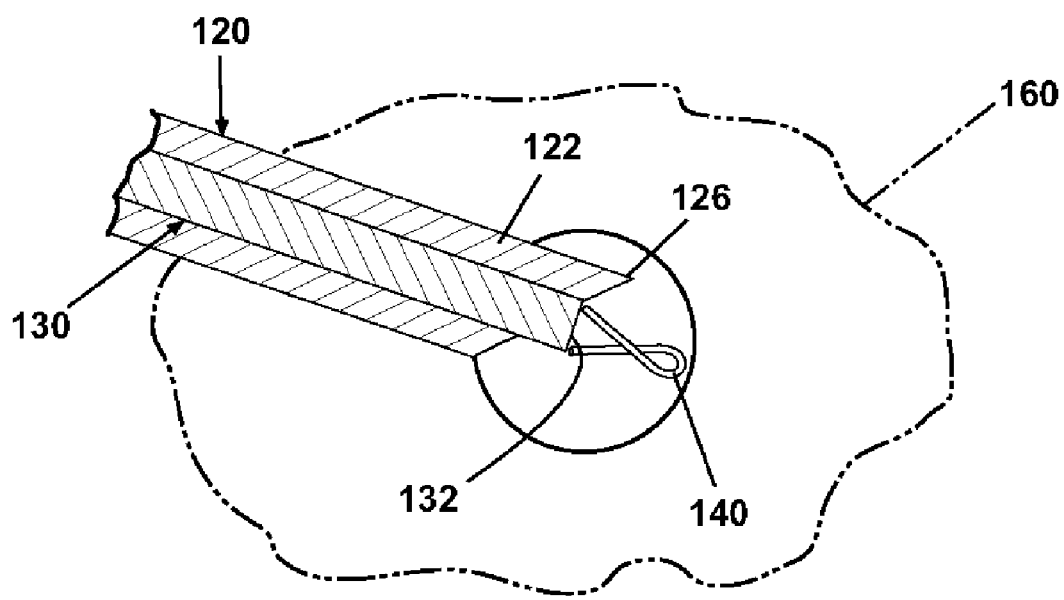
FIG. 11 is an enlarged view of the region labeled XI in FIG. 9.

With additional reference to FIGS. 7 and 11, the lumen 128 of the cannula 120 slidingly receives the stylet 130, which also comprises a proximal end 134 and a distal end 132. The stylet 130 is slidable from a ready position, wherein the distal end of the stylet 130 is spaced inwardly from the tip 126 to form a marker recess 129, as best viewed in FIG. 7, for housing an imaging marker 140, to an extended position, wherein the distal end 132 of the stylet 130 is advanced towards the tip 126 and into the marker recess 129 to reduce the volume of the marker recess 129 and thereby eject the imaging marker 140 from the marker recess 129, as shown in FIG. 11. It is preferred that the stylet 130 be sized in a manner such that when the stylet 130 is in the extended position, the stylet 130 extends to near the tip 126 of the cannula 120 to ensure complete ejection of the imaging marker 140 from the marker recess 129. Movement of the stylet 130 is controlled by the trigger 60.

Imaging markers are well known in the medical device art, and any suitable imaging marker can be utilized with the marking apparatus 10. Exemplary imaging markers are disclosed in U.S. Pat. No. 6,575,991, which is incorporated herein by reference in its entirety. Further, the type of imaging marker 140 is not limited by the size of the cannula 120; rather, the cannula 120 can be selected according to the type of imaging marker 140.

Referring again to FIGS. 1, 2, 6, and 6A, the trigger 60 comprises a slide 62, a button 76 disposed inside the slide 62 and movable relative to the slide 62, and a biasing member 86 for biasing the button 76 upward within the slide 62. The slide 62 comprises a substantially rectangular and elongated base 64 and a finger or thumb rest 66 extending upward from the base 64. Both sides of the rest 66 are undercut where the rest 66 meets the base 64 to form elongated channels 71 for slidingly mounting the trigger 60 to the flanges 36. The base 64 includes openings 70 located on each side of the rest 66 and underneath the channels 71 and a distal tab 72 sized to be received by the detent 112 in the cap 100. The rest 66, which is generally hollow for housing the button 76, has a top surface 67 contoured to conform to the fingers 152 or the thumb 156 and formed with an elongated aperture 68 extending therethrough. The base 64 further comprises a tubular stylet holder 74 on a side opposite the rest 66. The stylet holder 74 receives and fixedly mounts the stylet 130 to the trigger 60.

The button 76 comprises a base 78 and a fin 80 extending upward from the base 78 and sized for receipt within the elongated aperture 68 in the rest 66. The base 78 includes a proximal, upwardly extending flange 84 and distal, upwardly extending projections 82 sized for receipt in the openings 70 in the slide 62.

The biasing member 86 comprises a planar leaf spring 88 with a proximal, upwardly extending flange 90 and a pair of distal prongs 92. The leaf spring 88 and the flange 90 are oriented with an angle of less than 90 degrees therebetween. The angle is selected to optimize the amount of bias exerted against the button 76. Preferably, the angle between the leaf spring 88 and the flange 90 is about 83 degrees.

Figure 6:
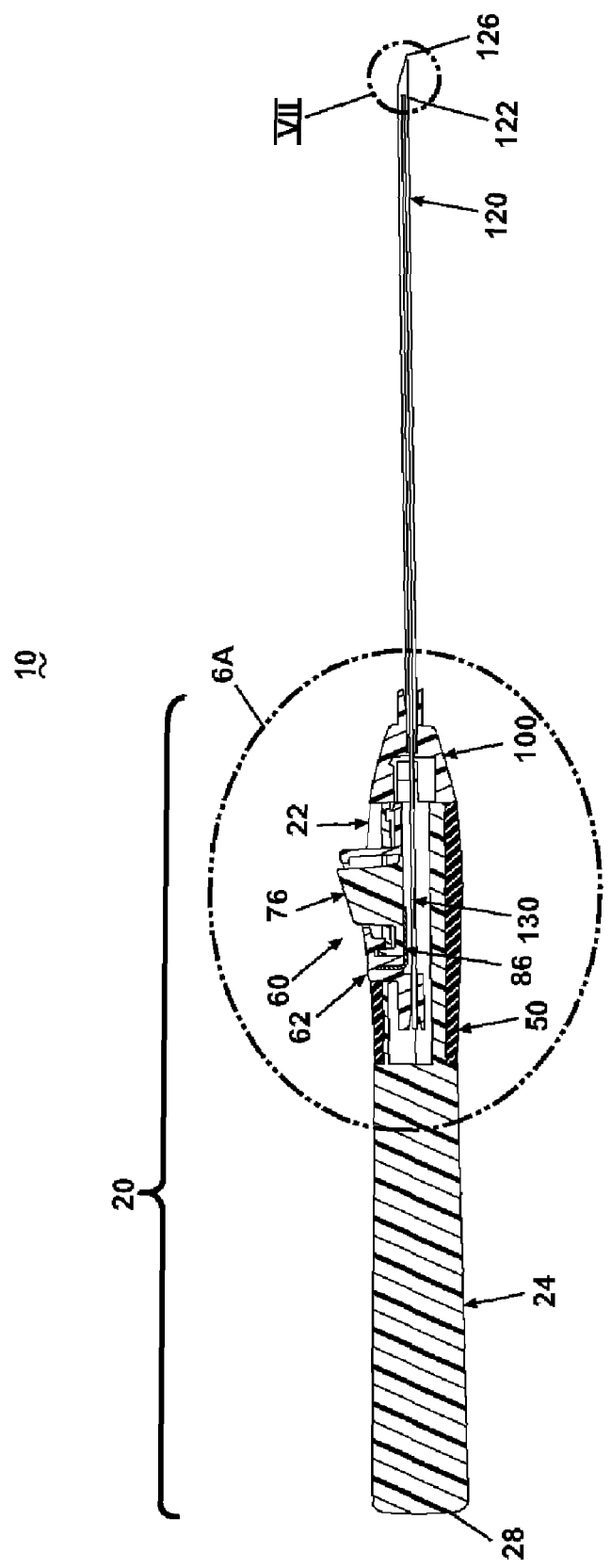
FIG. 6 is a sectional view taken along line 6-6 of FIG. 1.
Figure 6A:
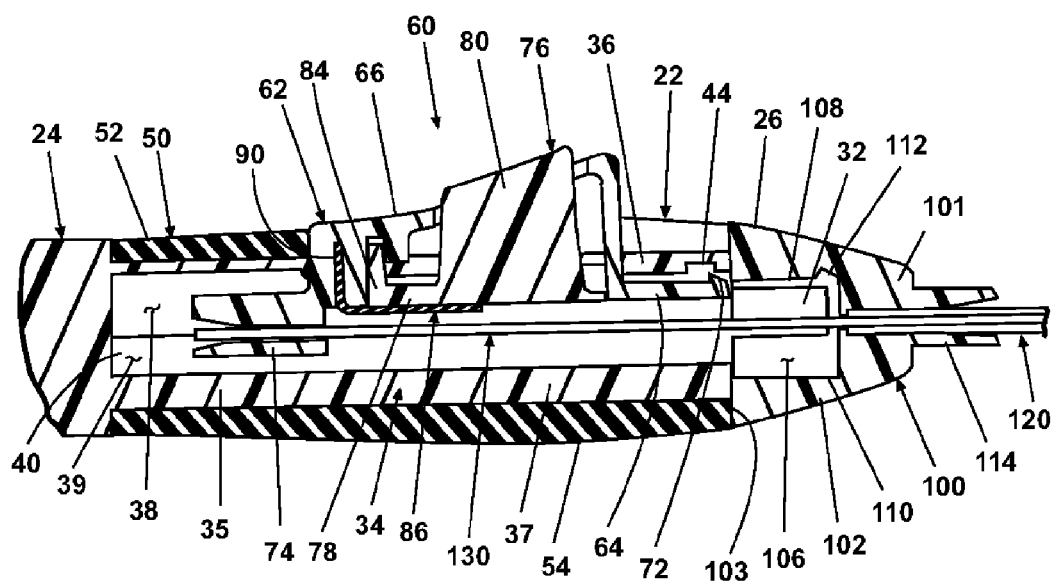
FIG. 6A is an enlarged sectional view of a front portion of the handle shown in FIG. 6.
Figure 8A:
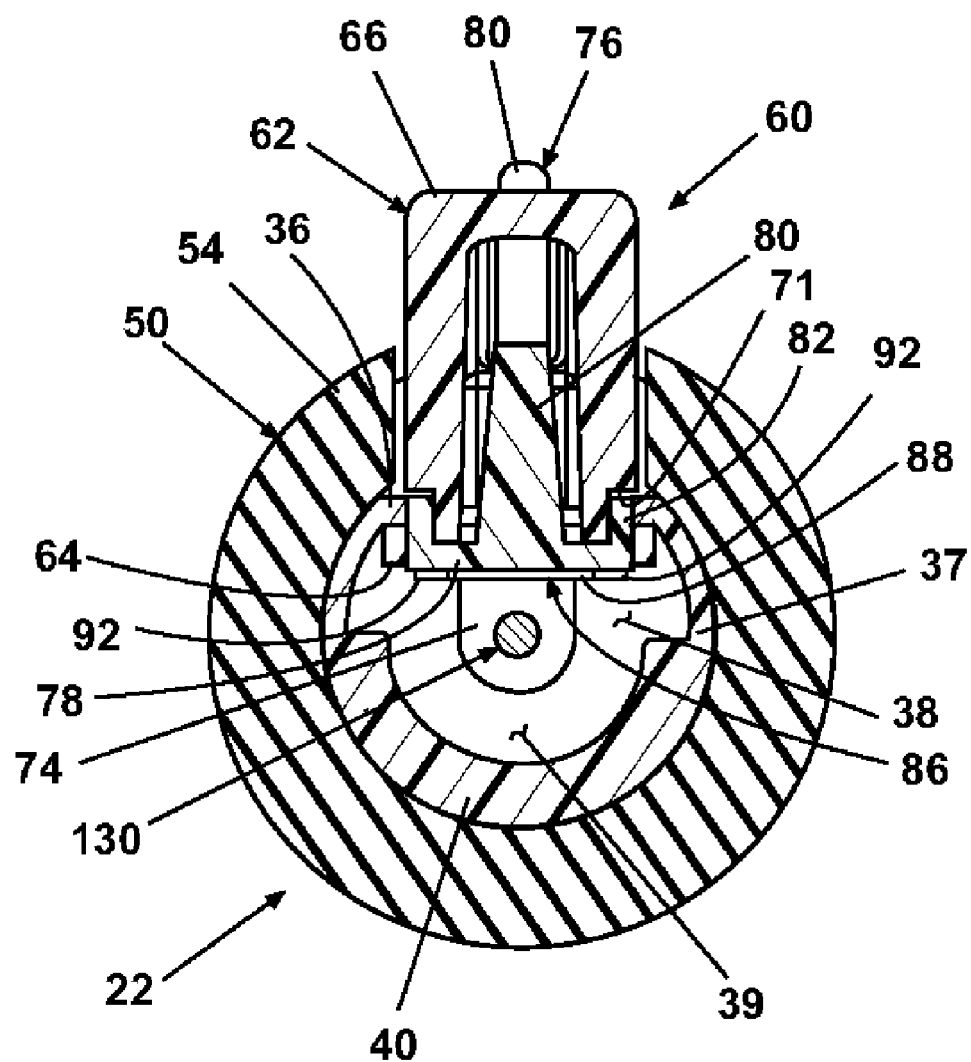
FIG. 8A is a sectional view taken along line 8A-8A of FIG. 8.

As best viewed in FIGS. 6A and 8A, in an assembled condition, the slide 62 houses the button 76, and the biasing member 86 is mounted to the slide 62 by the flange 90, which is inserted into a small cavity in the flange. The leaf spring 88 abuts the base 78 of the button 76 and biases the button 76 into the slide 62 such that the base 78 of the button 76 coincides with the base 64 of the slide 62, the fin 80 projects through the elongated aperture 68, and the projections 82 project through the openings 70 and into the channels 71. Downward force applied to the button 76 forces the button 76 downward against the bias of the biasing member 86. In this condition, the button 76 pivots about the flange 84, which is also inserted into a small cavity in the slide 62, the fin 80 is coincident with the top surface 67 of the rest 66, and the projections 82 move downward within the openings 70 and no longer reside within the channels 71.

Figure 10:
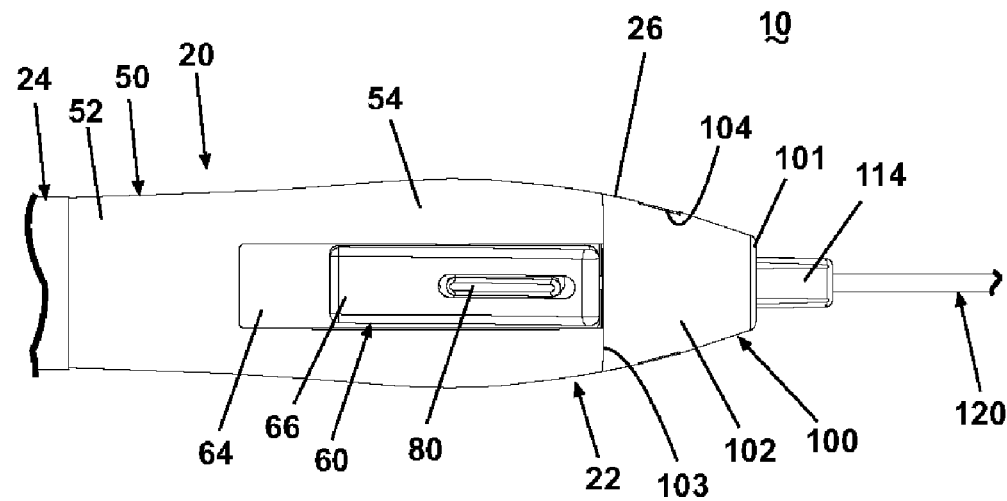
FIG. 10 is a top view of the marking apparatus shown in FIG. 9.
Figure 9:
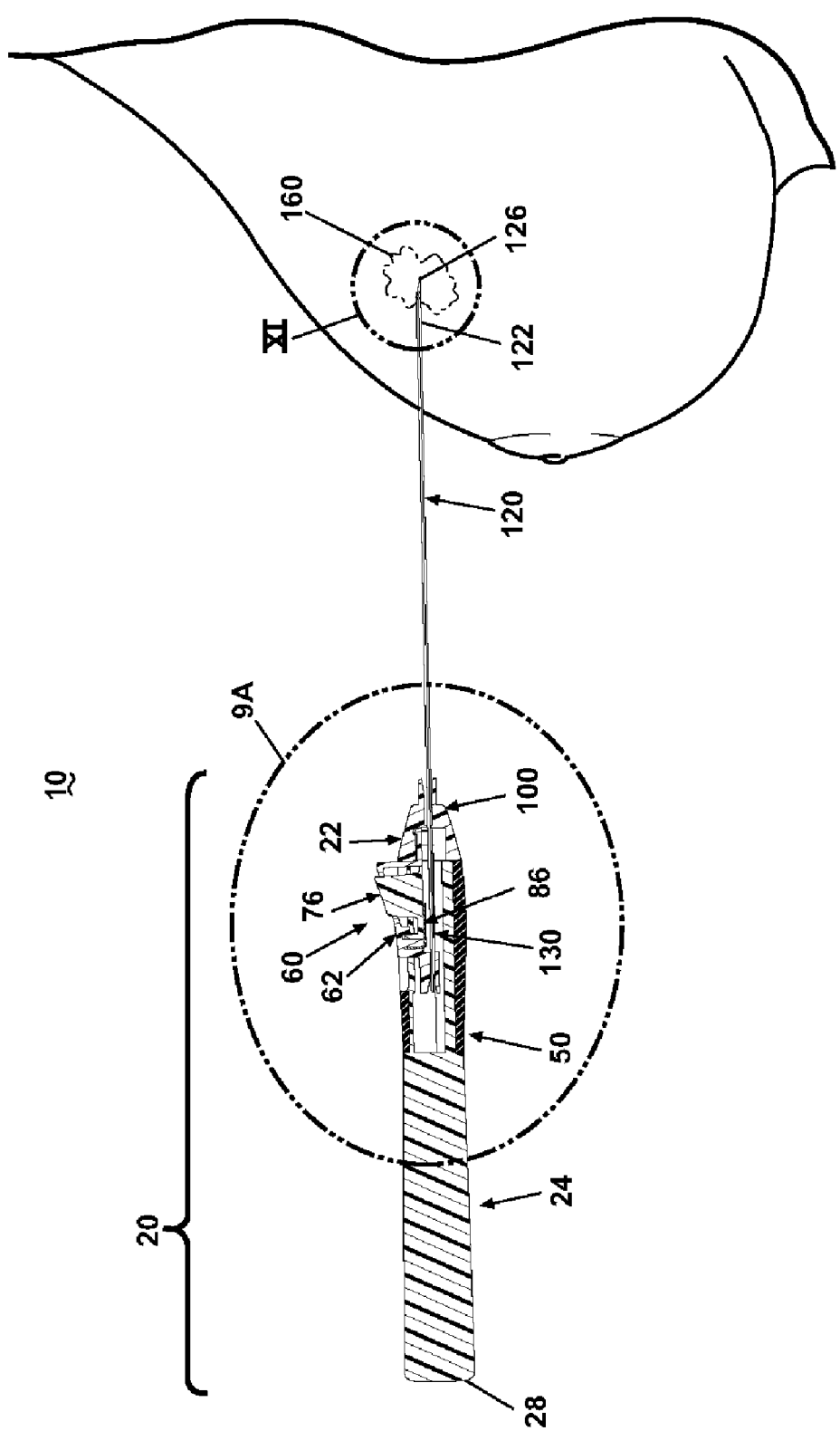
FIG. 9 is a partial sectional view of the marking apparatus shown in FIG. 1 with the trigger in a second position and wherein the marking apparatus is inserted into a tissue mass.
Figure 9A:
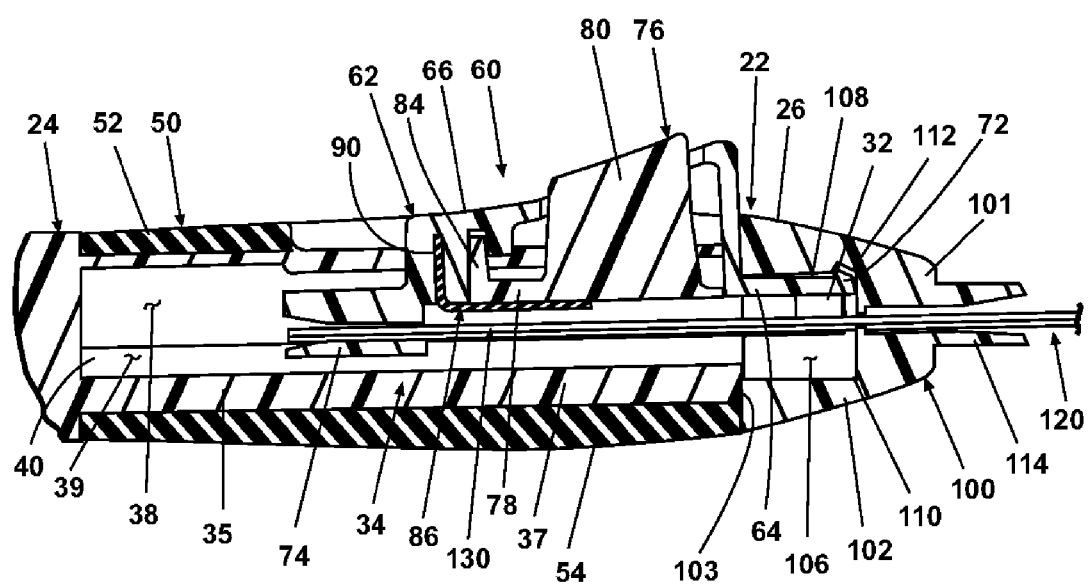
FIG. 9A is an enlarged sectional view of a front portion of the handle shown in FIG. 9.

When the trigger 60 is mounted to the handle 20, the flanges 36 on the handle 20 reside in the channels 71 on the trigger 60 whereby the trigger 60 can slide distally and proximally relative to the handle 20 between the first position and the second position. The rest 66 of the slide 62 and the fin 80 of the button 76 sit above the flanges 36, and the remaining portions of the trigger 60 reside in the cavity 38. The stylet holder 74 is located in the channel 39 defined by the curved lower wall 40 of the handle front portion 22. When the trigger 60 is in the first position, as shown in FIGS. 2-6A, 8, and 8A, the tab 72 is aligned with distal ends of the flanges 36, and the biasing member 86 biases the projections 82 into the first set of catches 42. The first set of catches 42 hold the projections 82 to retain the trigger 60 in the first position and to prevent sliding movement of the trigger 60. When the trigger is in the second position, as illustrated in FIGS. 9, 9A, and 10, the tab 72 is seated in the detent 112 in the cap 100, and the biasing member 86 biases the projections 82 into the second set of catches 44. Again, sliding movement of the trigger 60 is prevented because the projections 82 are held by the second set of catches 44. To move the trigger 60 between the first and second positions, downward force must be applied to the button 76 to disengage the projections 82 from the catches 42, 44. Because the stylet 130 is fixedly mounted to and moves with the trigger 60, the first and second positions of the trigger 60 correspond to the ready and extended positions of the stylet 130.

Referring now to FIGS. 3-5, because the trigger 60 extends from the front portion 22 of the handle 20, the marking apparatus 10 can be firmly held in a hand 150 while simultaneously moving the trigger 60 from the first position to the second position with the same hand 150. First, second, and third exemplary manners of holding the marking apparatus are illustrated in FIGS. 3-5, respectively. In the first manner, the handle 20 of the marking apparatus 10 is positioned between the fingers 152, preferably three fingers 152, and the palm 158 of the hand 150, and the thumb 156 is situated on the trigger 60 for actuation thereof. An index finger 154 preferably rests against the grip 50 for added stability. In the second manner, the marking apparatus 10 is positioned between the fingers 152, preferably three fingers 152, and the thumb 156 of the hand 150, and the index finger 154 is situated on the trigger 60. The rear portion 24 of the handle 20 can rest against a portion of the palm 158 for added stability. The third manner involves rotating the marking apparatus 180 degrees relative to its position in the first and second manners. The marking apparatus 10 is positioned between the fingers 152, preferably three fingers 152, and the palm 158 of the hand 150, and the index finger 156 is situated on the trigger 60. The thumb 156 preferably rests against the grip 50 for added stability. The three manners described above are exemplary, and the particular manner in which the marking apparatus 10 is held and actuated with the hand 150 can be determined by the user in accordance with the user's preferences.

An exemplary description of the operation of the marking apparatus 10 follows. It will be apparent to one of ordinary skill that the operation can proceed in any logical manner and is not limited to the sequence presented below. The following description is for illustrative purposes only and is not intended to limit the invention in any way.

To operate the marking apparatus 10, the user holds the marking apparatus 10 in the hand 150 in a preferred manner, such as in one of the three manners described above and shown in FIGS. 3-5. The marking apparatus 10 is in a condition shown in FIGS. 2-6A, 8, and 8A, wherein the trigger 60 is in the first position and, thus, the stylet 130 is in the ready position with the imaging marker 140 disposed within the marker recess 129. The marking apparatus 10 is inserted into a tissue mass 160, which is shown as a breast in FIG. 9. The user then guides the marking apparatus 10 to a predetermined site in the tissue mass 160 with the aid of an imaging system, such as an ultrasonic imaging system. For example, the user can hold an ultrasonic wand in a free hand (i.e., in a hand not holding the marking apparatus 10), and observe the location of the marking apparatus 10 in the tissue mass 160 on a video display monitor.

When the marking apparatus 10 is properly positioned with the tip 126 at the predetermined site in the tissue mass 160, the user moves the trigger 60 from the first position to the second position with the thumb 156 or the index finger 154 of the hand 150 while holding the marking apparatus 10 between the fingers 152 and the palm 158 or the fingers 152 and the thumb 156 of the same hand 150. In particular, the user depresses the fin 80 of the button 76 to push the button 76 against the bias of the biasing member 86. As a result, the projections 82 move downward within the openings 70 and no longer reside within the first set of catches 42 or the channels 71 and, therefore, no longer prevent sliding movement of the trigger 60. Once the button 76 is sufficiently depressed, the user maintains the downward force and applies a distal force to the trigger 60 to slide the trigger towards the second position. As the trigger 60 moves towards the second position, the tab 72 rides along the flat upper wall of the cap 100, and the projections 82 ride along the underside of the flanges 36. Further, the stylet 130 advances towards the tip 126 of the cannula 120 and into the marker recess 129 to thereby reduce the volume of the marker recess 129 and simultaneously push the imaging marker 140 distally towards the predetermined site.

When the trigger 60 reaches the second position, as shown in FIGS. 9, 9A, 10, and 11, the stylet 130 achieves the extended position for complete ejection of the imaging marker 140 from the marker recess 129. The tab 72 is received within the detent 112, the projections 82 are aligned with the second set of catches 44, and further distal movement of the trigger 60 is prevented by the cap 100. As the user removes the downward and distal forces, the button 76 moves upward within the rest 66 under the bias of the biasing member 86, and the projections 82 mate with the second set of catches 44 to retain the trigger 60 in the second position. The user then removes the marking apparatus 10 from the tissue mass with the hand 150. Because the trigger 60 is secured in the second position, accidental movement of the stylet 130 relative to the cannula 120 is prevented during withdrawal of the marking apparatus 10.

As described above, the location of the trigger 60 enables the user to firmly grasp the marking apparatus 10 in the hand 150 and simultaneously deploy the trigger 60 with the same hand 150 for ejection of the imaging marker 140 at the predetermined site. In addition, the location of the trigger 60 on the handle 20 gives the user a significant amount of control when positioning the tip 126 of the cannula 120. For example, when the marking apparatus 10 is inserted into the tissue mass 160, any movement of the handle 20 external to the tissue mass 160 induces similar movement of the cannula 120 inside the tissue mass 160. In other words, the marking apparatus 10 effectively pivots about the point where the marking apparatus 10 is inserted into the tissue mass 160. Because the trigger 60 extends from the front portion 22 of the handle 20, the distance from the pivot point to the trigger 60 is smaller when compared to prior art marking apparatuses having the trigger disposed at a proximal end of a handle 20. As the distance between the trigger 60 and the pivot point decreases, the ability of the user to keep the marking apparatus 10 steady or to control movement of the marking apparatus 10 increases.

The exemplary hand positions enabled by the front trigger are inherently more natural and sustainable than what was possible with prior art rear trigger devices. With most rear trigger devices, the practitioner grips the handle in the same manner that one would grip a knife for stabbing so that the practitioner's thumb would be able to actuate the rear trigger. Such a grip is best suited for moving the device distally to place the device within the tissue mass. However, it is more common for the practitioner to move the device laterally during insertion into the tissue mass. Most practitioners find it difficult and awkward to accurately laterally insert the device using the prior art rear trigger devices.

The inventive device permits the user to comfortably and accurately insert the cannula into the tissue mass and hold the device in the inserted position with great stability while the practitioner positions the tip of the cannula using the imaging system. The shape of the inventive device enhances the stability and positioning by providing a relative long handle area over which the user can apply opposing compressive forces between the fingers and the palm or the extended thumb.

While the invention has been specifically described in connection with certain specific embodiments thereof, it is to be understood that this is by way of illustration and not of limitation, and the scope of the appended claims should be construed as broadly as the prior art will permit.

What is claimed is:

1. A subcutaneous marking apparatus for placement of an imaging marker at a predetermined site in a tissue mass to facilitate subsequent determination of the predetermined site, the marking apparatus comprising:
   a handle having a front portion and a rear portion located behind the front portion, with the rear portion having a length such that a user can grasp the handle between multiple fingers and a palm or a thumb of one hand;
   a cannula defining a lumen and having a proximal end mounted to the handle and a distal end defining a tip;

a stylet slidably received within the lumen for movement between a ready position in which a distal end of the stylet is spaced inwardly from the tip to form a marker recess between the distal end of the stylet and the tip, and an extended position in which the distal end of the stylet is advanced toward the tip and into the marker recess;

a trigger extending through a side surface of the front portion of the handle, in a direction substantially perpendicular to an axis of the cannula, and operably engaging the stylet, the trigger being operable between a first position and a second position for moving the stylet between the ready position and the extended position; and an imaging marker disposed within the marker recess;

wherein at least a first portion of the trigger is moved downwardly in a direction substantially perpendicular to the axis of the cannula to release the trigger for movement from the first position to the second position; and wherein the marking apparatus can place the imaging marker at the predetermined site by the user actuating the trigger between the first and second positions with either an index finger or the thumb of the one hand while holding the handle between either the fingers and the thumb or the fingers and the palm to move the stylet from the ready position to the extended position to thereby eject the imaging marker from the marker recess after the tip of the cannula is located at the predetermined site.

2. The marking apparatus of claim 1 wherein the trigger is slidably mounted to the front portion such that sliding the trigger serves to operate the trigger between the first and second positions.

3. The marking apparatus of claim 2 wherein the trigger is connected to the stylet, the trigger and the stylet moving in unison as the trigger is moved between the first and second positions.

4. The marking apparatus of claim 3 and further comprising a first detent to hold the trigger in one of the first and second positions.

5. The marking apparatus of claim 4 and further comprising a second detent for holding the trigger in the other of the first and second positions.

6. The marking apparatus of claim 1 wherein the handle is grasped by at least three fingers of the one hand.

7. The marking apparatus of claim 1 wherein the stylet is fixedly mounted to the trigger such that movement of the trigger is directly transferred to movement of the stylet.

8. The marking apparatus of claim 1 wherein the trigger comprises at least one projection and the handle further comprises at least one catch sized to receive the at least one projection to retain the trigger in at least one of the first and second positions.

9. The marking apparatus of claim 8 wherein the trigger further comprises a biasing member that biases the at least one projection into the at least one catch to thereby prevent movement of the trigger from the at least one of the first and second positions.

10. The marking apparatus of claim 1 wherein the handle further comprises a resilient grip on the front portion.

11. A subcutaneous marking apparatus for placement of an imaging marker at a predetermined site in a tissue mass to facilitate subsequent determination of the predetermined site, the marking apparatus comprising:

a handle to be grasped by one hand of a user and comprising a front portion and a rear portion;

a cannula defining a lumen and having a proximal end mounted to the handle and a distal end defining a tip;

a stylet slidably received within the lumen for movement between a ready position in which a distal end of the stylet is spaced inwardly from the tip to form a marker recess between the distal end of the stylet and the tip, and an extended position in which the distal end of the stylet is advanced toward the tip and into the marker recess;

a trigger extending through a side surface of the front portion of the handle, in a direction substantially perpendicular to an axis of the cannula, and connected to the stylet, the trigger being movable between a first position and a second position for moving the stylet between the ready position and the extended position; and an imaging marker disposed within the marker recess;

wherein at least a first portion of the trigger is moved downwardly toward an interior of the handle to release the trigger for movement from the first position to the second position; and wherein the marking apparatus can place the imaging marker at the predetermined site by the user actuating the trigger between the first and second positions with either an index finger or a thumb of the one hand to move the stylet from the ready position to the extended position to thereby eject the imaging marker from the marker recess after the tip of the cannula is located at the predetermined site.

12. The marking apparatus of claim 11 wherein the trigger is slidably mounted to the front portion such that sliding the trigger serves to operate the trigger between the first and second positions.

13. The marking apparatus of claim 12 and further comprising a first detent to hold the trigger in one of the first and second positions.

14. The marking apparatus of claim 13 and further comprising a second detent for holding the trigger in the other of the first and second positions.

15. The marking apparatus of claim 11 wherein the handle is grasped between either fingers and the thumb or the fingers and a palm of the one hand.

16. The marking apparatus of claim 15 wherein the handle is grasped by at least three fingers of the one hand.

17. The marking apparatus of claim 11 wherein the stylet is fixedly mounted to the trigger such that movement of the trigger is directly transferred to movement of the stylet.

18. The marking apparatus of claim 11 wherein the trigger comprises at least one projection and the handle further comprises at least one catch sized to receive the at least one projection to retain the trigger in at least one of the first and second positions.

19. The marking apparatus of claim 18 wherein the trigger further comprises a biasing member that biases the at least one projection into the at least one catch to thereby prevent movement of the trigger from the at least one of the first and second positions.

20. The marking apparatus of claim 11 wherein the handle further comprises a resilient grip on the front portion.

21. A subcutaneous marking apparatus for placement of an imaging marker at a predetermined site in a tissue mass to facilitate subsequent determination of the predetermined site, the marking apparatus comprising:

a handle having a front portion and a rear portion located behind the front portion, the front portion including a hollow elongate body having a pair of inwardly extending flanges, the rear portion having a length such that a user can grasp the handle;

a cannula defining a lumen and having a proximal end mounted to the handle and a distal end defining a tip;

a stylet slidably received within the lumen for movement along an axis of the cannula between a ready position in which a distal end of the stylet is spaced inwardly from the tip to form a marker recess between the distal end of the stylet and the tip, and an extended position in which the distal end of the stylet is advanced toward the tip and into the marker recess; and a trigger configured for manual manipulation by a user, the trigger having a pair of channels slidably received by the inwardly extending flanges of the hollow elongate body to mount the trigger to the front portion of the handle, the trigger being operably engaged with the stylet such that the trigger and the stylet move linearly in unison as the stylet is moved between the ready position and the extended position by a corresponding manual sliding movement of the trigger along the inwardly extending flanges between a first position and a second position.

22. The marking apparatus of claim 21, wherein the pair of inwardly extending flanges includes a first set of catches and a second set of catches that are engaged by a portion of the trigger to retain the trigger in the first position and the second position, respectively.

* * * * *